(12) United States Patent
Challener et al.

(10) Patent No.: US 11,492,903 B2
(45) Date of Patent: Nov. 8, 2022

(54) SYSTEMS AND METHODS FOR ENTHALPY MONITORING OF A FLUID

(71) Applicant: General Electric Company, Schenectady, NY (US)

(72) Inventors: William Albert Challener, Glenville, NY (US); Emad Andarawis Andarawis, Ballton Lake, NY (US); David Milford Shaddock, Troy, NY (US); Sameer Dinkar Vartak, Bangalore (IN)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 559 days.

(21) Appl. No.: 16/600,049

(22) Filed: Oct. 11, 2019

(65) Prior Publication Data
US 2021/0108505 A1 Apr. 15, 2021

(51) Int. Cl.
| | | |
|---|---|---|
| E21B 49/08 | (2006.01) | |
| E21B 47/06 | (2012.01) | |
| G01N 25/02 | (2006.01) | |
| E21B 36/04 | (2006.01) | |
| G01K 17/00 | (2006.01) | |

(Continued)

(52) U.S. Cl.
CPC .......... *E21B 49/0875* (2020.05); *E21B 36/04* (2013.01); *E21B 47/06* (2013.01); *G01N 25/02* (2013.01); *E21B 49/08* (2013.01); *G01K 13/00* (2013.01); *G01K 17/00* (2013.01); *G01N 27/04* (2013.01); *G01N 2021/1761* (2013.01); *G01N 2021/8405* (2013.01)

(58) Field of Classification Search
CPC ...... E21B 36/04; E21B 47/06; E21B 49/0875; G01N 25/02
See application file for complete search history.

(56) References Cited

U.S. PATENT DOCUMENTS

| | | |
|---|---|---|
| 6,995,360 B2 | 2/2006 | Jones et al. |
| 7,328,624 B2 | 2/2008 | Gysling et al. |

(Continued)

OTHER PUBLICATIONS

Glantschnig, Werner J., et al.; "Light Scattering from Water Droplets in the Geometrical Optics Approximation", Applied Optics, vol. 20, No. 14, Jul. 15, 1981, 11 pages.

(Continued)

*Primary Examiner* — Jill E Culler
(74) *Attorney, Agent, or Firm* — Fletcher Yoder, P.C.

(57) ABSTRACT

A system includes a downhole tool having a housing and a passage extending through the housing, where the passage includes an inlet configured to receive a flow of a wellbore fluid and an outlet configured to discharge the flow of the wellbore fluid. The downhole tool includes a heating element configured to heat the flow of the wellbore fluid and to enable the flow of the wellbore fluid to transition to a single-phase fluid flow within the passage. The downhole tool includes a phase composition sensor positioned adjacent the passage and configured to provide feedback indicative of formation of the single-phase fluid flow. The system includes a controller configured to monitor a power consumption of the heating element and to determine an enthalpy of the wellbore fluid based in part on the power consumption and the feedback from the phase composition sensor.

20 Claims, 5 Drawing Sheets

(51) Int. Cl.
 G01K 13/00 (2021.01)
 G01N 27/04 (2006.01)
 G01N 21/84 (2006.01)
 G01N 21/17 (2006.01)

(56) References Cited

U.S. PATENT DOCUMENTS

| | | | |
|---|---|---|---|
| 7,637,167 | B2 | 12/2009 | Monmont et al. |
| 8,070,840 | B2 | 12/2011 | Diaz et al. |
| 8,616,282 | B2 | 12/2013 | Moscato et al. |
| 10,648,301 | B2 * | 5/2020 | Landi .................. F03B 17/061 |
| 2016/0320280 | A1 | 11/2016 | Kerr et al. |
| 2018/0051553 | A1 * | 2/2018 | Indo .................. E21B 49/10 |
| 2018/0058209 | A1 * | 3/2018 | Song .................. E21B 47/107 |
| 2018/0245463 | A1 * | 8/2018 | Shako .................. G01N 9/26 |

OTHER PUBLICATIONS

Wolceshyn, G.E., et al.; "Measurement of Steam Quality, Mass Flow Rate, and Enthalpy Delivery Rate Using Combined Neutron Densitometer and Nozzle", SPE Enhanced Oil Recovery Symposium in Tulsa, OK on Apr. 20-23, 1986; 12 pages.

Wang, N.N., et al.; "Optical Measurement of Wet Steam in Turbines", Journal of Engineering for Gas Turbines and Power, vol. 120, Oct. 1998, 5 pages.

Mitra, Chayan, et al.; "Development of Steam of Quality Measurement and Monitoring Technique Using Absorption Spectroscopy with Diode Lasers", IEEE Sensors Journal, vol. 11, No. 5, May 2011, 6 pages.

Juliusson, Egill "An investigation of Void Fraction and Dispersed-phase Velocity Measurement Techniques," Proc. 31th Workshop Geotherm. Res. Eng., Stanford University, Stanford, CA (2006), 78 pages.

Partin, J.K., et al.; "Development of Optical Technologies for Monitoring Moisture and Particulate in Geothermal Steam," Report for U.S. D.O.E. (2006) contract DE-AC07-05ID14517, 34 pages.

Atalay, Nilufer, et al; "Downhole Enthalpy Measurement with Fiber Optics," Proc. 33rd Workshop Geotherm. Res. Egn. (2008) SGP-TR-185, 45 pages.

Kolovratnik, Michal, et al.; "Wet steam wetness measurement in a 10 MW steam turbine," EPJ Web Conf. 67 (2014) 02055, 4 pages.

* cited by examiner

SYSTEMS AND METHODS FOR ENTHALPY MONITORING OF A FLUID

BACKGROUND

The subject matter disclosed herein relates to monitoring enthalpy of a fluid, and more specifically, to monitoring enthalpy of a fluid flowing through a wellbore.

Heated fluid may be extracted from a geological formation by drilling a wellbore that extends from the surface of the earth to a fluid reservoir within the geological formation, and then pumping the heated wellbore fluid up to the surface through the wellbore. In some cases, the heated fluid may be directed to components of a fluid extraction system (e.g., a geothermal power plant) that are configured to extract energy (e.g., thermal energy) from the heated fluid and to generate electrical energy using the extracted energy. The amount of electrical energy that may be generated using the heated fluid may correspond to an enthalpy of the heated fluid, which is generally dependent on a phase composition (e.g., a ratio of liquid and vapor) of the fluid. The enthalpy of the fluid may vary based on a depth at which the fluid enters the wellbore. Time based changes in the wellbore due to rock fracturing or shifts in the phase composition of the fluid may also affect the enthalpy of the fluid. During well boring it is desirable to determine fluid enthalpy as a function of well depth. Unfortunately, measurement of fluid enthalpy at the surface of the wellbore does not provide adequate information to evaluate effects of subsurface changes in the fluid enthalpy along a depth of the wellbore. As such, wellbore operations conducted during and after boring of the wellbore may be executed less efficiently. Indeed, without subsurface enthalpy data of the wellbore fluid, an operator of the fluid extraction system may make decisions regarding the extraction of the heated fluid that do not improve an efficiency of the fluid extraction system.

BRIEF DESCRIPTION

Certain embodiments commensurate in scope with the original claims are summarized below. These embodiments are not intended to limit the scope of the claims, but rather these embodiments are intended only to provide a brief summary of possible forms of the claimed subject matter. Indeed, the claims may encompass a variety of forms that may be similar to or different from the embodiments set forth below.

In one embodiment, a system includes a downhole tool configured to be conveyed through a wellbore. The downhole tool includes a housing and a passage extending through the housing, where the passage includes an inlet configured to receive a flow of a wellbore fluid and an outlet configured to discharge the flow of the wellbore fluid. The downhole tool also includes a heating element configured to heat the flow of the wellbore fluid and to enable the flow of the wellbore fluid to transition to a single-phase fluid flow within the passage. The downhole tool further includes a phase composition sensor positioned adjacent the passage and configured to provide feedback indicative of formation of the single-phase fluid flow. The system also includes a controller communicatively coupled to the heating element and the phase composition sensor, where the controller is configured to monitor a power consumption of the heating element and to determine an enthalpy of the wellbore fluid based in part on the power consumption and the feedback from the phase composition sensor.

In another embodiment, a downhole tool configured to be conveyed through a wellbore includes a housing and a conduit extending through an interior of the housing. The conduit defines a passage having an inlet configured to receive a flow of a wellbore fluid and an outlet configured to discharge the flow of the wellbore fluid. The downhole tool also includes a heating element positioned within the passage and configured to heat the flow of the wellbore fluid to enable the flow of the wellbore fluid to transition to a single-phase fluid flow within the passage. The downhole tool further includes a phase composition sensor coupled to the conduit and configured to identify formation of the single-phase fluid flow within the conduit.

In another embodiment, a method includes conveying a downhole tool into a wellbore and directing a flow of a wellbore fluid from the wellbore through a passage of the downhole tool, where the wellbore fluid is a two-phase fluid when entering the passage. The method also includes heating the flow of the wellbore fluid via a heating element to transition the wellbore fluid from the two-phase fluid to a single-phase fluid, detecting formation of the single-phase fluid within the passage via a phase composition sensor positioned near the passage, and monitoring, via a controller, a power consumption used by the heating element to transition the wellbore fluid to the single-phase fluid. The method further includes determining, via the controller, an enthalpy of the wellbore fluid within the wellbore based in part on the power consumption and detection of the formation of the single-phase fluid.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As briefly discussed above, a wellbore may be drilled into a geological formation to enable the extraction of a heated wellbore fluid (e.g., water, brine solution) from a fluid reservoir within the geological formation. The extracted fluid may be used to perform work on components of a geothermal power plant or other fluid extraction system positioned near the surface of the geological formation. For example, the heated wellbore fluid may be used to drive rotation of a turbine system or other power generation device that is configured to generate electrical energy using the heated fluid.

In some cases, a pressure and/or a temperature of the heated fluid within the wellbore may be substantially high. Therefore, the fluid may exist in a two-phase state, in which the liquid state of the fluid and the gaseous state of the fluid co-exist. That is, in the two-phase state, portions of the fluid flowing along the wellbore may be in the liquid state, while other portions of the fluid may be in the gaseous state. A fluid within the two-phase state may have various phase compositions at a particular temperature and pressure, such that an actual phase composition of the fluid may not be determinable based on acquired temperate measurements and/or acquired pressure measurements of the fluid. For clarity, as used herein, the "phase composition" of a fluid refers to a ratio correlating an amount of the fluid that is in a liquid state or phase to an amount of fluid that is in a gaseous (e.g., vapor) state or phase.

As an example, in a first condition, at a particular temperature and pressure, a wellbore fluid (e.g., a two-phase wellbore fluid) may be approximately 10 percent liquid and approximately 90 percent vapor. Alternatively, in a second condition, at the same temperature and pressure, the wellbore fluid may be approximately 70 percent liquid and approximately 30 percent vapor. Fluids in the gaseous state typically have enthalpies that are greater than enthalpies of fluids in the liquid state. Accordingly, in the aforementioned example, an overall enthalpy of the wellbore fluid at the first condition may be greater than an overall enthalpy of the wellbore fluid at the second condition.

Unfortunately, because the particular phase composition of wellbore fluids within the wellbore is typically unknown, conventional fluid extraction systems may be ill-equipped to determine the enthalpy of the wellbore fluids being extracted from the wellbore. As a result, conventional fluid extraction system may inefficiently operate components (e.g., the turbine system) at the surface of the wellbore that are driven using the wellbore fluid, and that are adjusted and/or controlled based on the enthalpy of the extracted wellbore fluid.

It is now recognized that determining an enthalpy of the wellbore fluid within the wellbore, prior to extraction of the wellbore fluid from the wellbore, enables determination of whether to adjust components of a fluid extraction system in response to changes in downhole wellbore parameters. That is, it is now recognized that determining the enthalpy of the wellbore fluid in situ within the wellbore may facilitate monitoring downhole enthalpy changes to enable adjustment of fluid extraction components configured to receive the extracted wellbore fluid from the wellbore based on the enthalpy values of the wellbore fluid at various depths along the wellbore.

Accordingly, the disclosed techniques include systems and methods for determining an enthalpy of a fluid flowing through a wellbore drilled within a geological formation. In particular, embodiments of the present disclosure are directed toward a downhole tool that is configured to determine the enthalpy of a wellbore fluid, in situ, along a particular location of the wellbore. In this manner, the downhole tool enables determination of the enthalpy of the wellbore fluid prior to extraction of the wellbore fluid from the wellbore. It should be understood that, although the disclosed embodiments are discussed in the context of a fluid extraction system configured to extract a fluid from a geological formation, the embodiments of the present disclosure may also be implemented in a variety of other technological fields. As a non-limiting example, the techniques disclosed herein may be implemented on boiler systems, medical steam sterilizers, turbine systems, and other suitable fluid extraction and/or fluid purification systems.

Figure 1:
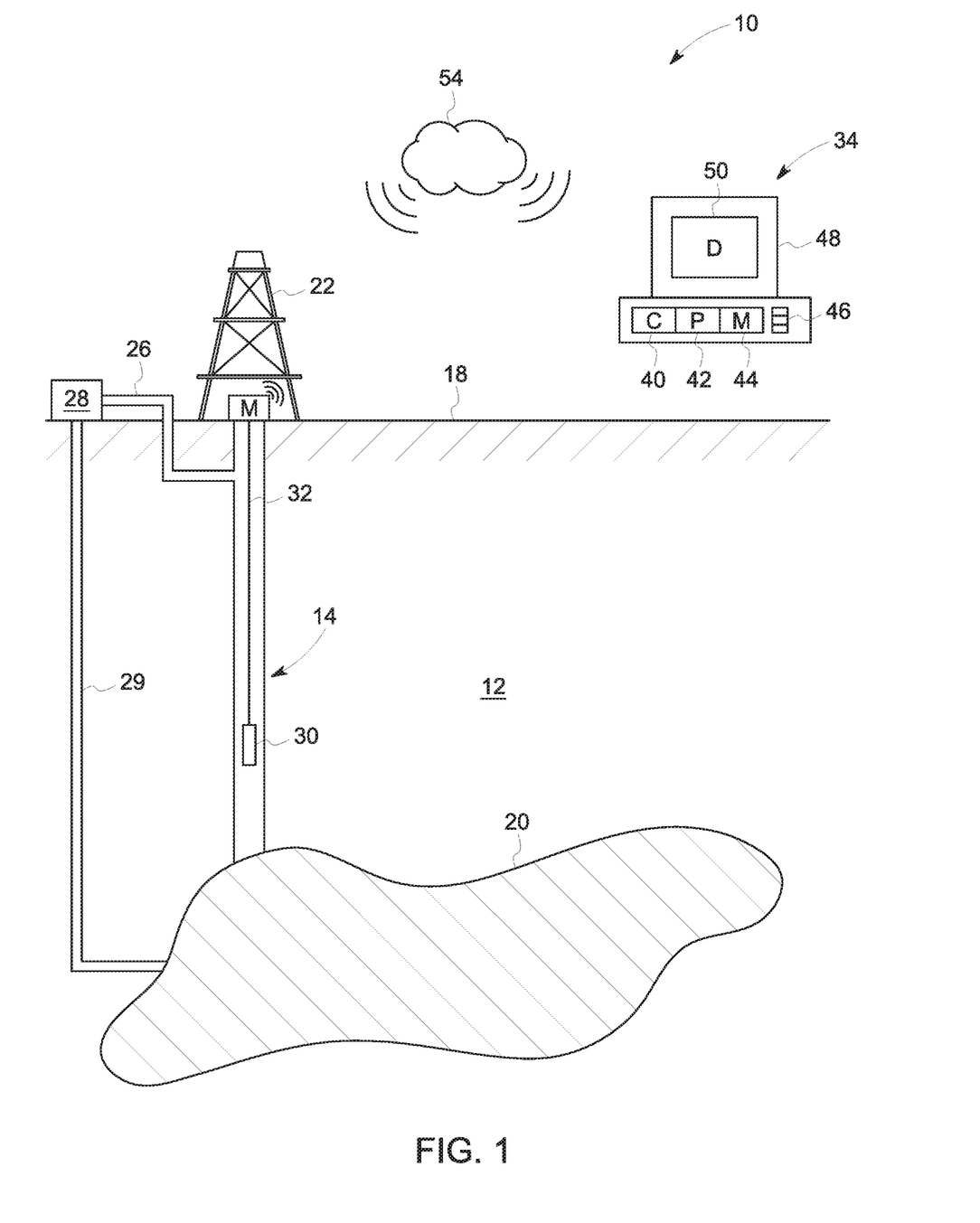
FIG. 1 is a schematic of an embodiment of a fluid extraction system having a downhole tool for measuring fluid characteristics within a wellbore, in accordance with an embodiment.

With the foregoing in mind, FIG. 1 is a schematic of an embodiment of a fluid extraction system 10. Wellbore fluids may be accessed from a geological formation 12 via a wellbore 14. For example, in some embodiments, the wellbore 14 may extend from a surface 18 of the earth to a reservoir 20 (e.g., a fluid reservoir) formed within the geological formation 12. Although the wellbore 14 extends generally vertically from the reservoir 20 to a fluid extraction rig 22 in the illustrated embodiment of FIG. 1, it should be appreciated that, in other embodiments, the wellbore 14 may extend at an angle oblique to the surface 18 or may change directions as it extends from the reservoir 20 to the fluid extraction rig 22. That is, the wellbore 14 may include portions that extend oblique to, perpendicular to, or parallel to the surface 18.

The fluid extraction rig 22 may extract (e.g., pump) fluid from the reservoir 20 or from other portions of the geological formation 12 toward the surface 18 via the wellbore 14. Suitable conduits or piping 26 may be fluidly coupled to the wellbore 14 and configured to direct the extracted wellbore fluid to a processing facility 28. The processing facility 28 may include, for example, a geothermal power plant or other power generation facility configured to extract thermal energy from the received wellbore fluid and to generate electrical energy using the extracted thermal energy. In some embodiments, the fluid extraction rig 22 may be included in the processing facility 28. In some embodiments, a supply conduit 29 (e.g., a casing) within another wellbore may enable the processing facility 28 to direct supply fluid (e.g., water, brine) to the reservoir 20 to replenish the extracted wellbore fluid. Accordingly, the supply fluid may be heated within the geological formation 12 and re-extracted from the geological formation 12 via the fluid extraction rig 22. That is, the supply fluid may be extracted from cracks or fissures within the geological formation 12 via the wellbore 14.

A downhole tool 30 may be inserted into the wellbore 14 using a cable 32 that is spooled or unspooled from a winch of the fluid extraction rig 22. In certain embodiments, a drill string may be used to raise or lower the downhole tool 30 along the wellbore 14 instead of the cable 32. In any case, the downhole tool 30 may include one or more sensor that are configured to measure fluid characteristics of the wellbore fluid within the wellbore 14. The sensors may send feedback indicative of the measured fluid characteristics to a computing system 34 (e.g., a controller, a computer, a tablet, a mobile device, etc.) that may be located on the surface 18. As will be discussed in detail below, the computing system 34 may be configured to determine an enthalpy of the wellbore fluid within the wellbore 14 based on the feedback provided via the sensors of the downhole tool 30.

As shown in the illustrated embodiment, the computing system 34 may include communication circuitry 40, a processor 42, a memory 44, communication ports 46, and a user interface 48, which may include a display 50. The processor 42 may include a microprocessor, which may execute software for controlling the components of the fluid extraction system 10, components of the processing facility 28, components of the downhole tool 30, and/or any other suitable components. The processor 42 may include multiple microprocessors, one or more "general-purpose" microprocessors, one or more special-purpose microprocessors, and/or one or more application specific integrated circuits (ASICS), or some combination thereof. For example, the processor 42 may include one or more reduced instruction set (RISC) processors. The memory 44 may include a volatile memory, such as random access memory (RAM), and/or a nonvolatile memory, such as read-only memory (ROM). The memory 44 may store information, such as control software, look up tables, configuration data, etc. For example, the memory 44 may store processor-executable instructions including firmware or software for the processor 42 execute, such as instructions for controlling any of the aforementioned components of the fluid extraction system 10. In some embodiments, the memory 44 is a tangible, non-transitory, machine-readable-medium that may store machine-readable instructions for the processor 42 to execute. The memory 44 may include ROM, flash memory, a hard drive, or any other suitable optical, magnetic, or solid-state storage medium, or a combination thereof.

Figure 2:
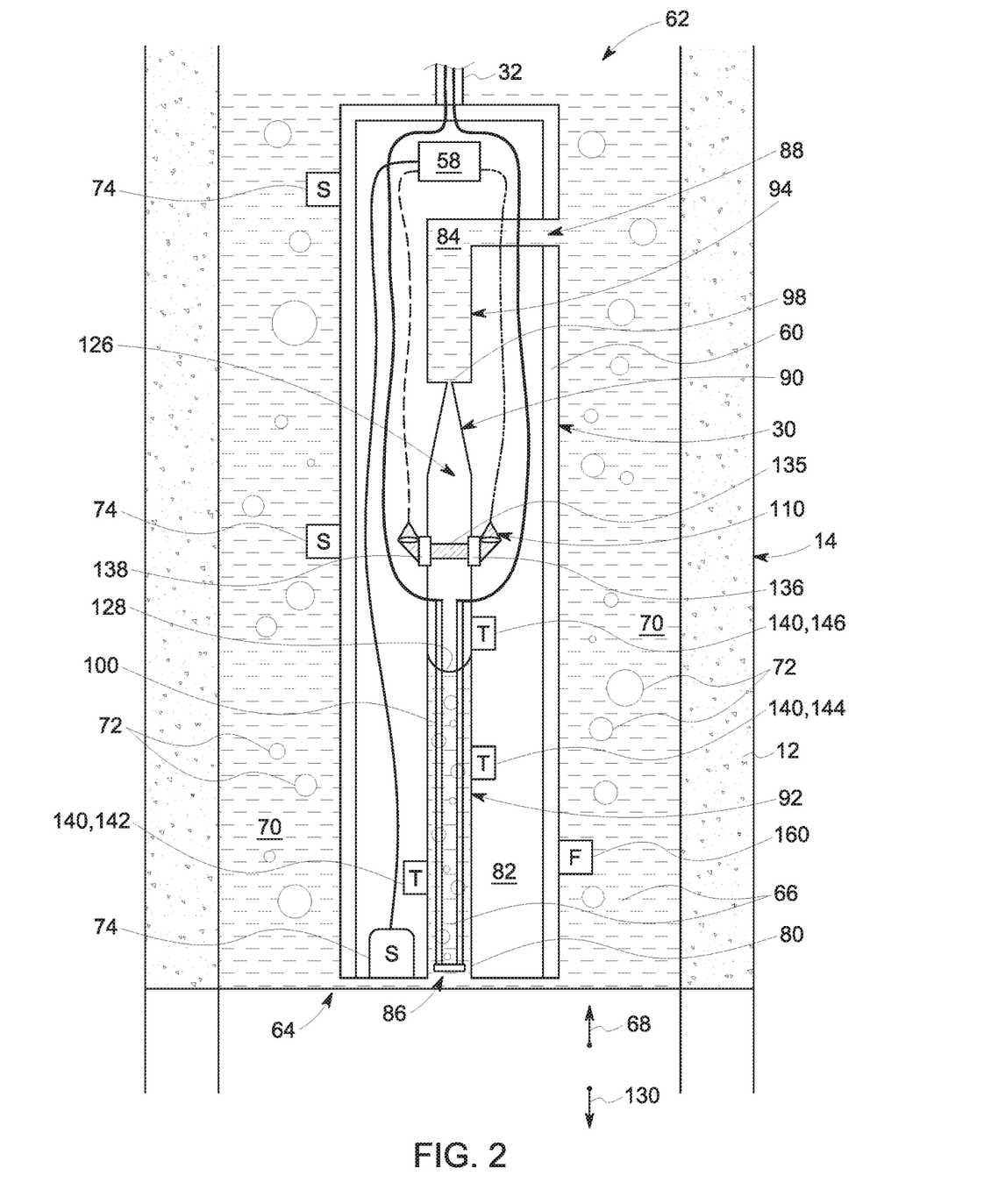
FIG. 2 is a schematic cross-sectional view of an embodiment of a downhole tool for measuring fluid characteristics within a wellbore, in accordance with an embodiment.

In some embodiments, suitable communication components (e.g., wires, fiber optic lines) may be integrated within the cable 32 and used to transfer signals between the downhole tool 30 and the computing system 34. Additionally or alternatively, data collected by the downhole tool 30 may be passed to the computing system 34 wirelessly (e.g., via a cloud network 54). In some embodiments, the computing system 34 is located remotely relative to the wellbore 14, and communications between the downhole tool 30 and the computing system 34 may be transferred via the cloud network 54 or via another suitable network. The computing system 34 may be configured to receive and analyze data from the downhole tool 30 in real-time. Moreover, the computing system 34 may be outfitted with software stored on the memory 44 and executed by the processor 42 to facilitate analysis of the collected data. For example, as discussed below, the computing system 34 may be capable of processing the data collected by the downhole tool 30 to determine an enthalpy of wellbore fluids at discrete locations along the wellbore 14. It should be noted that, in certain embodiments, some or all of the techniques discussed herein may be performed on a data processing system 58 (e.g., as shown in FIG. 2) included in the downhole tool 30 in addition to, or in lieu of, the computing system 24. Indeed, it should be understood that the data processing system 58 may include a dedicated processor and memory configured to facilitate execution of the techniques discussed herein.

FIG. 2 is a schematic cross-sectional view of an embodiment of the downhole tool 30 positioned within the wellbore 14. As shown in the illustrated embodiment, the downhole tool 30 includes a housing 60 (e.g., an enclosure) that extends from a first end portion 62 to a second end portion 64 of the downhole tool 30. The housing 60 is positioned within the wellbore 14 to enable wellbore fluid 66 to flow along the housing 60 in a downstream direction 68 from the reservoir 20 to the surface 18. That is, the wellbore fluid 66 may flow along the housing 60 from the second end portion 64 to the first end portion 62 of the housing 60. In some embodiments, the wellbore fluid 66 may include a two-phase fluid that includes a liquid component 70 and a gaseous (e.g., vapor) component 72. For example, at least a portion of the wellbore fluid 66 may include water that is between the saturated water line and the saturated vapor line on an pressure-enthalpy diagram, such that liquid water and steam may co-exist in the wellbore fluid 66. For clarity, it should be noted that the wellbore fluid 66 will also be referred to herein as a "two-phase wellbore fluid 66." In other words, the "two-phase wellbore fluid 66" may be indicative of wellbore fluid that includes both the liquid component 70 and the gaseous component 72.

As shown in the illustrated embodiment, the downhole tool 30 includes one or more sensors 74 that are configured to measure characteristics of the wellbore fluid 66. For example, the sensors 74 may include pressure sensors and/or temperature sensors that are configured to provide feedback to the computing system 34 and/or to the data processing system 58 indicative of the pressure of the wellbore fluid 66 and/or the temperature of the wellbore fluid 66. However, it should be understood that, in other embodiments, the sensors 74 may include a variety of other sensors configured to measure additional or alternate characteristics of the wellbore fluid 66. In some embodiments, the sensors 74 may be positioned at a particular location along the downhole tool 30, such as near the second end portion 64 of the downhole tool 30. In other embodiments, the sensors 74 may be distributed at various locations along the housing 60 of the downhole tool 30.

The downhole tool 30 includes a conduit 80 (e.g., a tube) that extends into an interior 82 of the downhole tool 30 to form a passage 84 though the housing 60. The passage 84 extends from an inlet 86 of the conduit 80 and terminates at an outlet 88 of the conduit 80. In some embodiments, the conduit 80 includes a converging section 90 that is positioned between an inlet section 92 (e.g., near the inlet 86) and an outlet section 94 (e.g., near the outlet 88) of the conduit 80. The converging section 90 may converge linearly or non-linearly in the downstream direction 68 from the inlet section 92 to the outlet section 94. Accordingly, the converging section 90 may define an orifice 98 that is positioned at an interface between the converging section 90 and the outlet section 94.

Indeed, a cross-sectional area of the converging section 90 may gradually decrease in the downstream direction 68 from the inlet section 92 to the orifice 98. As a non-limiting example, in some embodiments, a cross-sectional area of the orifice 98 may be between about 5 percent and about 40 percent of a cross-sectional area of the inlet section 92. In some embodiments, the cross-sectional area of the inlet section 92 and the cross-sectional area of the outlet section 96 may be substantially similar. In any case, the conduit 80 enables the wellbore fluid 66 to flow through the passage 84 in the downstream direction 68 from the inlet 86 to the outlet 88. In some embodiments, the conduit 80 is sized to enable laminar flow of the wellbore fluid 66 along the passage 84.

In certain embodiments, a screen (e.g., a filter) may be coupled to the inlet 86 of the conduit 80 and configured to block entry of foreign matter (e.g., mud, pebbles, certain organic matter) into the passage 84. As such, the screen may ensure that foreign matter suspended within the wellbore fluid 66 does not clog or otherwise obstruct the orifice 98 or other portions of the conduit 80 during operation of the downhole tool 30.

In the illustrated embodiment, a heating element 100 is disposed within inlet section 92. As discussed in detail below, the heating element 100 may include one or more heaters that are configured to heat the wellbore fluid 66 entering the conduit 80. For example, in some embodiments, the heating element 100 may include an electrical heater that is configured to convert electrical energy to thermal energy. The electrical energy used to operate the heating element 100 may be supplied via a battery module of the downhole tool 30 and/or via a power unit positioned at the surface 18. For example, power transmission lines may be integrated within the cable 32 to transfer electrical power from the power unit at the surface 18 to the downhole tool 30.

Although the heating element 100 is positioned within the passage 84 in the illustrated embodiment of FIG. 2, it should be understood that, in other embodiments, the heating element 100 may be positioned externally to the passage 84. For example, the heating element 100 may be positioned within the interior 82 of the downhole tool 30 and may be coupled to an outer surface (e.g., an outer circumference) of the conduit 80. In such embodiments, the heating element 100 may be configured to heat the inlet section 92 of the conduit 80 (e.g., via conductive heat transfer), such that the wellbore fluid 66 within the passage 84 may absorb thermal energy from the heated inlet section 92. Moreover, in certain embodiments, an insulating material (e.g., glass fiber) may be disposed within the interior 82 of the housing 60 and positioned about a circumference of the conduit 80. Accordingly, the insulating material may mitigate heat transfer from the heating element 100 to other components of the downhole tool 30 that may be positioned within the interior 82, such as elements of the data processing system 58.

The downhole tool 30 includes a phase composition sensor 110 that is coupled to, for example, the inlet section 92. The phase composition sensor 110 may be communicatively coupled to, and configured to provide feedback to, the computing system 34, the data processing system 58, or both. Particularly, as discussed below, the phase composition sensor 110 may be configured to provide feedback indicating whether the wellbore fluid 66 within certain portions of the conduit 80 has a two-phase composition or a single-phase composition, such as a single-phase composition in which the wellbore fluid 66 is substantially gaseous (e.g., more than 95 percent gas per unit mass). In some embodiments, the downhole tool 30 may include an additional phase composition sensor that is positioned within or along a portion of the outlet section 94.

Figure 3:
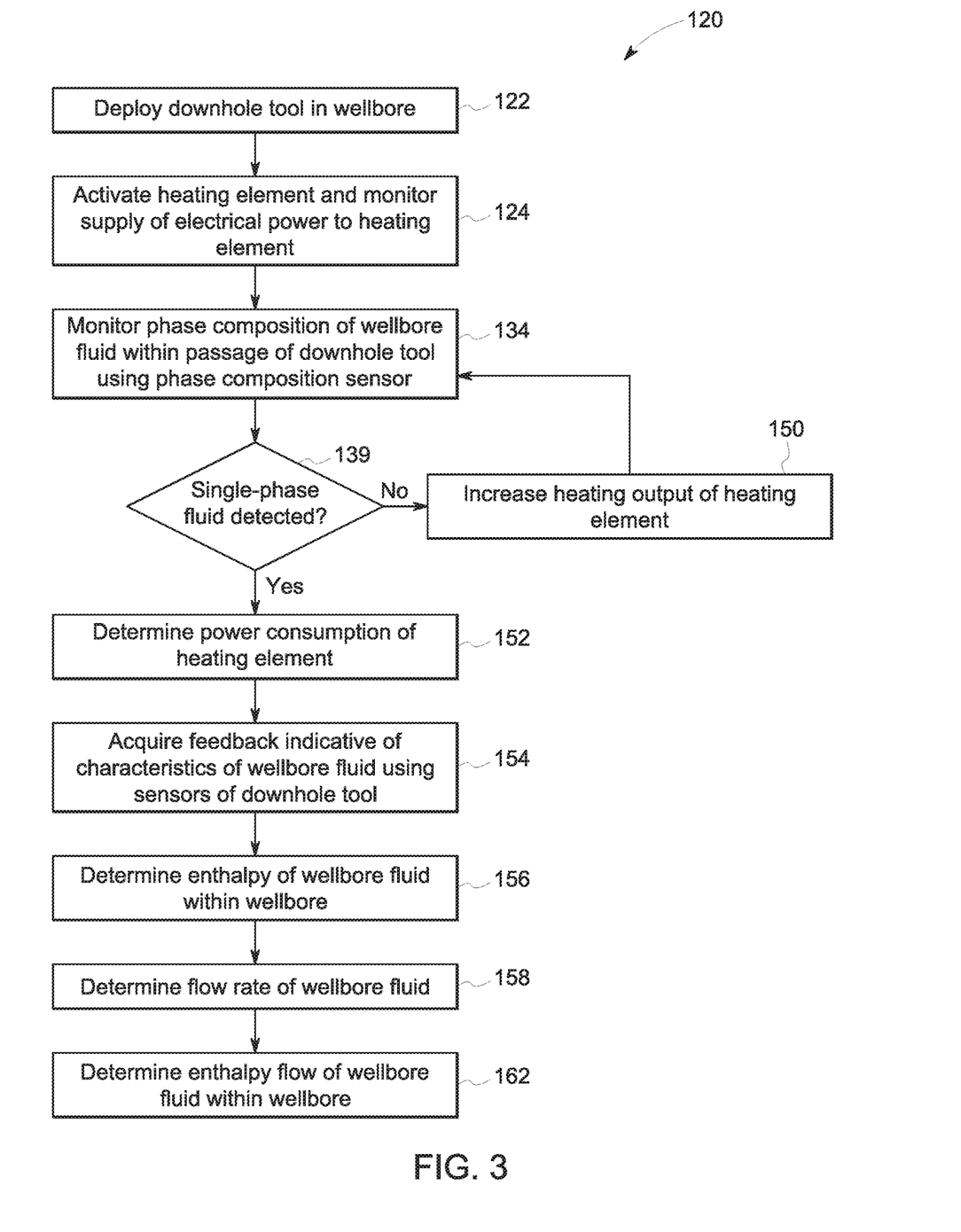
FIG. 3 is a flow chart of a process for determining an enthalpy of a wellbore fluid flowing though a wellbore using a downhole tool, in accordance with an embodiment.

FIG. 3 is flow diagram of an embodiment of a process 120 that may be used to control the downhole tool 30 to facilitate determining an enthalpy of the wellbore fluid 66 within the wellbore 14. FIG. 3 will be referred to concurrently with FIG. 2 throughout the following discussion. It should be noted that the steps of the process 120 discussed below may be performed in any suitable order and are not limited to the order shown in the illustrated embodiment of FIG. 3. Moreover, it should be noted that additional steps of the process 120 may be performed, and certain steps of the process 120 may be omitted. In some embodiments, the process 120 may be executed on the processor 42, on a processor of the data processing system 58, and/or on any other suitable processor of the fluid extraction system 10. The process 120 may be stored on, for example, the memory 44, a memory of the data processing system 58, and/or on any other suitable memory of the fluid extraction system 10.

The process 120 may begin with deploying the downhole tool 30 in the wellbore 14, as indicated by block 122. For example, the fluid extraction rig 22 may be operable to position the downhole tool 30 at a particular location (e.g., depth) within the wellbore 14 using the cable 32 or another suitable conveyance device (e.g., a drill pipe of a dill string). As discussed above, the wellbore fluid 66 may be extracted from the geological formation 12, such that the wellbore fluid 66 flows through the wellbore 14 in the downstream direction 68 toward the surface 18. Accordingly, when the downhole tool 30 is deployed within the wellbore 14, the wellbore fluid 66 may flow into the passage 84 in the downstream direction 68. Particularly, the wellbore fluid 66 may flow into the conduit 80 via the inlet 86, flow along the inlet section 92, the converging section 90, and the outlet section 94, and discharge from the conduit 80 via the outlet 88. It should be appreciated that, when initially deploying the downhole tool 30 within the wellbore 14, the wellbore fluid 66 flowing through the conduit 80 and along the passage 84 may have a two-phase composition that includes the liquid component 70 and the gaseous component 72.

The process 120 includes activating the heating element 100 and monitoring a supply of electrical power (e.g., in watts) to the heating element 100, as indicated by block 124. For example, as discussed above, electrical energy may be supplied to the heating element 100 via a power unit positioned on the surface 18 and/or via a battery module of the downhole tool 30 to enable the heating element 100 to heat the wellbore fluid 66 within the conduit 80. That is, the heating element 100 may enable wellbore fluid 66 traveling along the inlet section 92 of the conduit 80 to absorb thermal energy from the heating element 100, thus heating the wellbore fluid 66. The computing system 34 may be configured to record (e.g., log) a power consumption of the heating element 100 or receive feedback from the heating element 100 indicative of the power consumption of the heating element 100.

As discussed in detail below, the heating element 100 may enable the wellbore fluid 66 traveling through the conduit 80 to absorb sufficient thermal energy to transition from the two-phase composition having both the liquid component 70 and the gaseous component 72 to a single-phase wellbore fluid 126 that is in the gaseous phase. That is, the single-phase wellbore fluid 126 may include a substantially large gaseous component 72 (e.g., more than 95 percent per unit mass) and a substantially negligible liquid component 70 (e.g., less than 5 percent per unit mass). The wellbore fluid 66 within the conduit 80 may transition from the two-phase composition to the singe-phase wellbore fluid 126 at an interface 128. In other words, the interface 128 may define a boundary within the conduit 80 that separates the two-phase wellbore fluid 66 within the conduit 80 from the single-phase wellbore fluid 126 (e.g., the gaseous wellbore fluid) within the conduit 80. However, it should be appreciated that, in some embodiments, the interface 128 may include a region of fluid positioned between the two-phase wellbore fluid 66 and the single-phase wellbore fluid 126 instead of a boundary.

In some embodiments, when activating the heating element 100, formation of the single-phase wellbore fluid 126 may begin near the orifice 98. The orifice 98 may enable a flow of the single-phase wellbore fluid 126 to discharge from the converging section 90 into the outlet section 94. The orifice 98 may throttle (e.g., reduce, regulate) a flow of the single-phase wellbore fluid 126 into the outlet section 94, such that the single-phase wellbore fluid 126 may accumulate (e.g., increase in quantity) within the converging section 90 during operation of the heating element 100.

In some embodiments, the single-phase wellbore fluid 126 may condense within the outlet section 94 to return back to the two-phase wellbore fluid 66. In some embodiments, the orifice 98 may ensure that a pressure of the single-phase wellbore fluid 126 flowing through the orifice 98 in the downstream direction 68 is greater than a pressure within the outlet section 94. Accordingly, the orifice 98 may ensure that fluid flow from the outlet section 94 into the converging section 90 is substantially mitigated or blocked. That is, the orifice 98 may facilitate blocking a flow of the two-phase wellbore fluid 66 in an upstream direction 130, opposite to the downstream direction 68, from the outlet section 94 back into the converging section 90.

As the heating element 100 gradually heats the wellbore fluid 66 within the inlet section 92 and/or the converging section 90, the amount of single-phase wellbore fluid 126 within the conduit 80 may increase, such that the interface 128 gradually moves from the orifice 98 toward the phase composition sensor 110. As discussed below, in some embodiments, the phase composition sensor 110 may be able detect formation of the single-phase wellbore fluid 126 based on identification of the interface 128. The phase composition sensor 110 may provide feedback indicating the formation of the single-phase wellbore fluid 126 to, for example, the computing system 34. Accordingly, the phase composition sensor 110 may enable monitoring of a phase composition of the wellbore fluid 66 within the passage 84, as indicated by block 134.

For example, in some embodiments, the phase composition sensor 110 may include a light sensor that is configured to project a light beam 135 across the passage 84 and through the wellbore fluid 66 flowing along the passage 84. For example, the light sensor may include an emitter 136 (e.g., positioned at a first side of the passage 84) configured to generate and project the light beam 135 and a receiver 138 (e.g., positioned at a second, opposing side of the passage 84) configured to detect the light beam 135. The light sensor may be configured to measure scattering of the light beam 135 as the light beam 135 travels through the wellbore fluid 66 flowing along the passage 84. The degree of scattering of the light beam 135 may be relatively large when the light beam 135 is projected through the two-phase wellbore fluid 66. Indeed, bubbles of the gaseous component 72 suspended within the liquid component 70 of the wellbore fluid 66 may cause the light beam 135 to reduce in intensity (e.g., due to scattering) when traveling through the wellbore fluid 66 from the emitter 136 to the receiver 138. Conversely, the degree of scattering of the light beam 135 may be relatively small when the light beam 135 is projected through the single-phase wellbore fluid 126. In some embodiments, a reduction in the light intensity (e.g., a differential between the intensity of light emitted by the emitter 136 and the intensity of light received by the receiver 138) of the light beam 135, when traveling through the single-phase wellbore fluid 126, may be known or empirically determined, and may be associated with a threshold value. Accordingly, the light sensor may indicate that the interface 128 has traveled past (e.g., in the upstream direction 130) the light beam 135 upon determining that the reduction in light intensity between the emitter 136 and the receiver 138 is equal to or less than the threshold value. As such, feedback from the light sensor may be used for detecting formation of the single-phase wellbore fluid 126 within the passage 84, as indicated by block 139.

In some embodiments, the phase composition sensor 110 may include a plurality of temperature sensors 140 that may be used in addition to, or in lieu of, the light sensor to detect the single-phase wellbore fluid 126 at the block 139. For example, a temperature of the two-phase wellbore fluid 66 within the conduit 80 may remain substantially constant as the two-phase wellbore fluid 66 absorbs thermal energy from the heating element 100. Instead of increasing in temperature when absorbing thermal energy from the heating element 100, the two-phase wellbore fluid 66 may be converted from the liquid component 70 to the gaseous component 72. In contrast, the single-phase wellbore fluid 126, when absorbing thermal energy from the heating element 100, does indeed increase in temperature. As a result, the wellbore fluid 66 within the conduit 80 may include a relatively constant temperature profile between the inlet 86 and the interface 128, while a temperature profile of the single-phase wellbore fluid 126 increases or fluctuates between the interface 128 and the orifice 98. In other words, the interface 128 may define a change in the temperature gradient of the wellbore fluid 66 along the inlet section 92 and/or the converging section 90.

In some embodiments, the temperature sensors 140 may be configured to measure and monitor the temperature gradient along the conduit 80. Accordingly, the temperature sensors 140 may be used to detect the single-phase wellbore fluid 126 at the block 139 via detection of the interface 128. For example, the temperature sensors 140 may provide feedback indicating that respective temperature values measured by a first temperature sensor 142 and a second temperature sensor 144 are relatively low and equal to one another, while a temperature value measured by a third temperature sensor 146 is relatively large. Accordingly, based on such sensor feedback, the computing system 34 may determine that the interface 128 is positioned between the second and third temperature sensors 144, 146, and thus, detect formation of the single-phase wellbore fluid 126 within the passage 84.

In some embodiments, the single-phase wellbore fluid 126 may be detected by measuring a dielectric constant of the fluid within the conduit 80 in addition to, or in lieu of, the techniques discussed above. For example, in some embodiments, a dielectric constant of the two-phase wellbore fluid 66 may be relatively large (e.g., between a value of about 40 and 60) and may fluctuate as the two-phase wellbore fluid 66 is heated by the heating element 100. A dielectric constant of the single-phase wellbore fluid 126 may be relatively low (e.g., between a value of about 0.5 and 2). Accordingly, existence of the single-phase wellbore fluid 126 may be detected using, for example, a capacitance sensor that is configured to measure the dielectric constant of fluid in the conduit 80 at a particular location along the conduit 80. That is, the capacitance sensor may detect the single-phase wellbore fluid 126 upon determining that a dielectric constant of fluid, at a particular location along the conduit 80 (e.g., near or at the interface 128), is equal to or below a threshold value associated with an expected dielectric constant of the single-phase wellbore fluid 126.

In some embodiments, the single-phase wellbore fluid 126 may be detected by measuring a resistivity (e.g., an electrical resistivity) of the fluid within the conduit 80 in addition to, or in lieu of, the techniques discussed above. For example, in some embodiments, the two-phase wellbore fluid 66 may include a resistivity that is relatively low (e.g., due to dissolved ions within the liquid component 70 of the two-phase wellbore fluid 66). Conversely, the single-phase wellbore fluid 126 in the vapor phase may include a resistivity that is relatively high. Accordingly, existence of the single-phase wellbore fluid 126 may be detected using, for example, a resistivity sensor that is configured to measure the resistivity of fluid in the conduit 80 at a particular location along the conduit 80. That is, the resistivity sensor may detect the single-phase wellbore fluid 126 upon determining that a resistivity of fluid, at a particular location along the conduit 80 (e.g., near or at the interface 128), is equal to or above a threshold value associated with an expected resistivity of the single-phase wellbore fluid 126.

In certain embodiments, if formation of the single-phase wellbore fluid 126 is not detected at the block 139 after lapse of a predetermined time interval, the computing system 34 may increase a heating output of the heating element 100, as indicated by block 150. In some embodiments, the computing system 34 may iteratively repeat blocks 134, 139, and 150 (e.g., after lapse the predetermined time interval) until formation of the single-phase wellbore fluid 126 is detected or until a heating output of the heating element 100 reaches an upper threshold value.

Upon detection of the single-phase wellbore fluid 126 at the block 139, the computing system 34 may determine a quantity of heat that has been output by the heating element 100 to induce formation of the single-phase wellbore fluid 126. For example, the computing system 34 may determine the heating output of the heating element 100 by determining a power consumption (e.g., a logged electrical power consumption) of the heating element 100, as indicated by block 152.

The computing system 34 may acquire feedback indicative of certain characteristics of the wellbore fluid 66 via the sensors 74 of the downhole tool 30, as indicated by block 154. For example, the sensors 74 may provide the computing system 34 with feedback indicative of a pressure of the wellbore fluid 66 and/or a temperature of the wellbore fluid 66 at the location of the downhole tool 30 within the wellbore 14. The computing system 34 may, based on the acquired sensor feedback from the sensors 74 and the power consumption of the heating element 100 (e.g., as determined at the block 152), determine the enthalpy of the wellbore fluid 66 within the wellbore 14, as indicated by block 156. In particular, the computing system 34 may implement algorithms (e.g., correlations) to determine the enthalpy of the wellbore fluid 66 based on the power consumption of the heating element 100 involved to induce formation of the single-phase wellbore fluid 126, and the measured temperature of the wellbore fluid 66 within the wellbore 14 and/or the measured pressure of the wellbore fluid 66 within the wellbore 14. In some embodiments, the computing system 34 may determine the enthalpy of the wellbore fluid 66 in real-time. Accordingly, the computing system 34 may adjust operation of components of the fluid extraction system 10 based on the determined enthalpy of the wellbore fluid 66.

In some embodiments, the computing system 34 may determine an enthalpy flow rate of the wellbore fluid 66 based on the determined enthalpy of the wellbore fluid 66 and a measured flow rate of the wellbore fluid 66. For example, as indicated by block 158, the downhole tool 30 may include one or more flow rate sensors 160 that are configured to measure a flow rate of the wellbore fluid 66 relative to the geological formation 12 and/or to measure a flow rate of the wellbore fluid 66 through the conduit 80. As indicated by block 162, the computing system 34 may determine the enthalpy flow rate of the wellbore fluid 66 based on the measurements acquired by the flow rate sensors 160 and the determined enthalpy of the wellbore fluid 66.

In some embodiments, a flow rate of the wellbore fluid 66 through the conduit 80 may be determined based on feedback from the temperature sensors 140 in addition to, or on lieu of, the feedback acquired by the flow rate sensors 160. For example, to determine a flow rate through the conduit 80 using the temperature sensors 140, the heating element 100 may first heat the conduit 80 to a threshold temperature, and may be deactivated upon heating the conduit 80 to the threshold temperature. One of more of the temperature sensors 140 may be used to determine a cooling rate of the conduit 80 upon deactivation of the heating element 100. For example, feedback from the temperature sensors 140 may be used to determine a time interval that lapses until the conduit 80 cools to a target temperature, such as a temperature of the wellbore fluid 66 surrounding the downhole tool 30. As such, this time interval may be used determine a flow rate of the wellbore fluid 66 through the conduit 80.

For example, if the flow rate of wellbore fluid 66 through the conduit 80 is relatively large, the wellbore fluid 66 may absorb thermal energy from the conduit 80 at a rate that is faster than a rate at which the wellbore fluid 66 absorbs thermal energy from the conduit 80 when a flow rate of the wellbore fluid 66 through the conduit 80 is relatively small. Accordingly, when flowing through the conduit 80 at the relatively high flow rate, the wellbore fluid 66 may cool the conduit 80 to the target temperature in a time interval that is less than a time interval involved in cooling the conduit 80 to the target temperature when the flow rate of the wellbore fluid 66 is relatively low. The computing system 34 may, via a correlation between measured or known characteristics (e.g., density, physical composition) of the wellbore fluid 66 and the time interval involved to cool the conduit 80 by a particular temperature range, determine the flow rate of the wellbore fluid 66 through the conduit 80.

Figure 4:
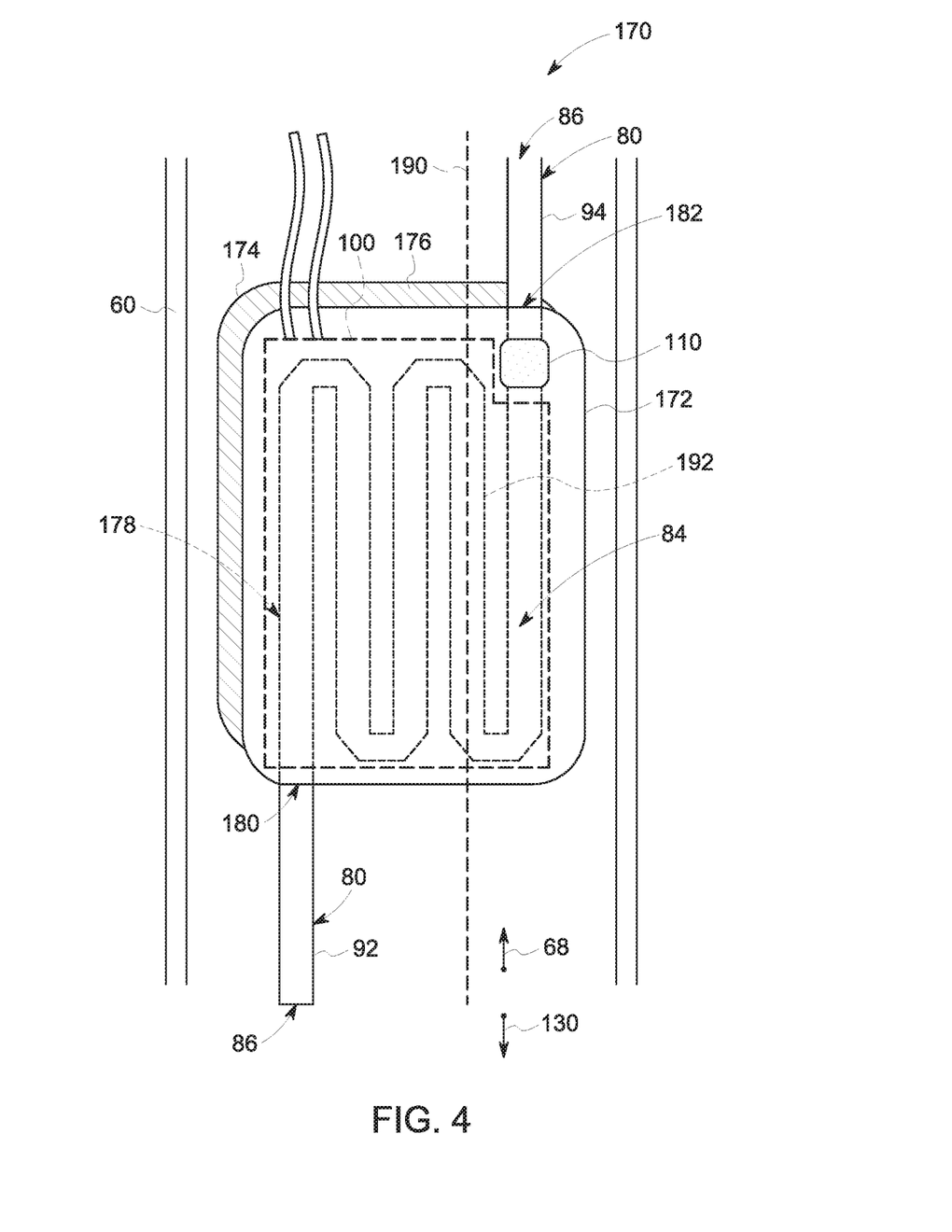
FIG. 4 is a front view of an embodiment of a downhole tool for measuring fluid characteristics within a wellbore, in accordance with an embodiment.
Figure 5:
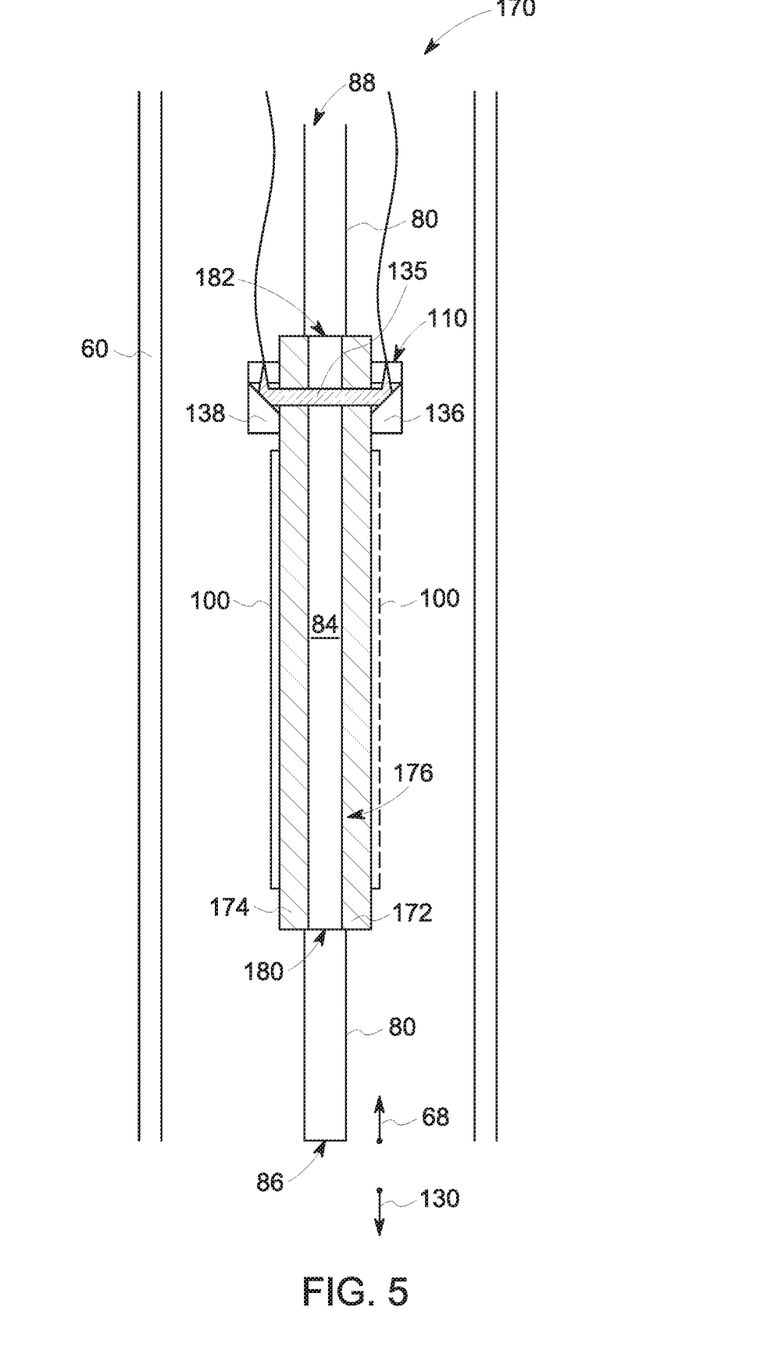
FIG. 5 is a side view of an embodiment of a downhole tool for measuring fluid characteristics within a wellbore, in accordance with an embodiment.

FIG. 4 is a front view of another embodiment of the downhole tool 30. In particular, FIG. 4 illustrates a downhole tool 170 in which the passage 84 is formed between a first sheet 172 and a second sheet 174 of the downhole tool 30. FIG. 5 is a side view of an embodiment of the downhole tool 170. FIGS. 4 and 5 will be discussed concurrently below.

In some embodiments, the downhole tool 30 may include an inner body 176 that is disposed within the housing 60. The inner body 176 includes a path 178 (e.g., a serpentine path) formed therein, and may be positioned between the first sheet 172 and the second sheet 174 that are configured to sealingly engage with the inner body 176 to form the passage 84. Accordingly, the passage 84 may extend in a serpentine manner from a first end portion 180 of the passage 84 to a second end portion 182 of the passage 84. In some embodiments, a first portion (e.g., the inlet section 92) of the conduit 80 may be coupled to the first end portion 180 of the passage 84 and form a portion of the passage 84, and a second end portion (e.g., the outlet section 94) of the conduit 80 may be coupled to the second end portion 182 of the passage 84 and form an additional portion of the passage 84. Accordingly, the wellbore fluid 66 may flow through the passage 84 from the inlet 86 of the conduit 80 to the outlet 88 of the conduit 80. As a non-limiting example, in certain embodiments, an inner diameter of the passage 84 may be between about 0.5 milliliters and 2.5 millimeters.

In some embodiments, the first sheet 172, the second sheet 174, or both, may be formed from a transparent piece of material. As a non-limiting example, the first sheet 172 and/or the second sheet 174 maybe formed from sapphire, silicon, or silicon carbide. The heating element 100 may be coupled to the first sheet 172, the second sheet 174, or both, and may be operable to heat (e.g., via conductive heat transfer through the sheets 172 and/or 174) the wellbore fluid 66 flowing through the passage 84. The phase composition sensor 110 may be coupled to and/or integrated with the first and second sheets 172, 174. Accordingly, the phase composition sensor 110 may detect formation of the single-phase wellbore fluid 126 within the passage 84 in accordance with the techniques discussed above.

For example, the single-phase wellbore fluid 126 may enter the passage 84 at the inlet 86 as the two-phase wellbore fluid 66. The heating element 100 may heat the two-phase wellbore fluid 66 as the two-phase wellbore fluid 66 flows along the passage 84, and thus, may enable the two-phase wellbore fluid 66 to transition to the single-phase wellbore fluid 126. Accordingly, the phase composition sensor 110 may detect the formation of the single-phase wellbore fluid 126 at or near the second end portion 182 of the passage 84. As an example, in some embodiments, the phase composition sensor 110 may include the light sensor discussed above, which may be configured to project the light beam 135 through the first sheet 172, the second sheet 174, and the wellbore fluid 66 flowing between the first and second sheets 172, 174. As such, the light sensor may detect formation of the single-phase wellbore fluid 126 by monitoring a degree of scattering of the light beam 135.

In some embodiments, the light sensor may be positioned at opposing ends of the inner body 176 to enable the light sensor to project the light beam 135 along a length 190 of a channel 192 of the passage 84. The channel 192 may include a channel of a plurality of channels that collectively form the serpentine path of the passage 84. In such embodiments, the inner body 176 may be formed from a transparent material (e.g., sapphire, silicon, silicon carbide) to enable the light beam 135 to pass through the inner body 176 (e.g., from the emitter 136 positioned at a first end of the inner body 176 to the receiver 138 positioned at a second end of the inner body 176).

As set forth above, embodiments of the present disclosure may provide one or more technical effects useful for determining an enthalpy of a wellbore fluid prior to extraction of the wellbore fluid from the wellbore. In particular, embodiments of the present disclosure facilitate measuring an enthalpy and/or an enthalpy flow rate of a wellbore fluid in situ within the wellbore. It should be understood that the technical effects and technical problems in the specification are examples and are not limiting. Indeed, it should be noted that the embodiments described in the specification may have other technical effects and can solve other technical problems.

This written description uses examples to disclose the claimed subject matter, including the best mode, and also to enable any person skilled in the art to practice the disclosed subject matter, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a downhole tool configured to be conveyed through a wellbore, comprising:
   a housing;
   a passage extending through the housing and having an inlet configured to receive a flow of a wellbore fluid and an outlet configured to discharge the flow of the wellbore fluid;
   a heating element configured to heat the flow of the wellbore fluid and enable the flow of the wellbore fluid to transition to a single-phase fluid flow within the passage; and
   a phase composition sensor positioned adjacent the passage and configured to provide feedback indicative of formation of the single-phase fluid flow; and
   a controller communicatively coupled to the heating element and the phase composition sensor, wherein the controller is configured to monitor a power consumption of the heating element, and to determine an enthalpy of the wellbore fluid based in part on the power consumption and the feedback from the phase composition sensor.

2. The system of claim 1, wherein the passage includes an inlet section, a converging section, and an outlet section, wherein the inlet section extends from the inlet to the converging section, the converging section terminates at an orifice, and the outlet section extends from the orifice to the outlet.

3. The system of claim 2, wherein a cross-sectional area of the orifice is less than a cross-sectional area of the outlet section.

4. The system of claim 1, wherein the passage extends through an interior of the housing along a serpentine path.

5. The system of claim 1, wherein the heating element is positioned within the passage.

6. The system of claim 1, wherein the phase composition sensor comprises a light sensor, a plurality of temperature sensors, a capacitance sensor, or a resistivity sensor.

7. The system of claim 1, wherein the passage is formed between a first transparent sheet and a second transparent sheet in fluid communication with the passage.

8. The system of claim 7, wherein the heating element is coupled to the first transparent sheet, the second transparent sheet, or both, and the phase composition sensor is coupled to the first transparent sheet and the second transparent sheet and configured to project a light beam though the first transparent sheet, the passage, and the second transparent sheet.

9. The system of claim 1, comprising one or more auxiliary sensors configured to provide the controller with additional feedback indicative of a pressure of the wellbore fluid, a temperature of the wellbore fluid, or both, wherein the controller is configured to determine the enthalpy of the wellbore fluid based on the power consumption, the feedback from the phase composition sensor, and the additional feedback from the one or more auxiliary sensors.

10. The system of claim 1, wherein the downhole tool comprises the controller.

11. A downhole tool configured to be conveyed through a wellbore, comprising:
    a housing;
    a conduit extending through an interior of the housing and defining a passage having an inlet configured to receive a flow of a wellbore fluid and an outlet configured to discharge the flow of the wellbore fluid;
    a heating element positioned within the passage and configured to heat the flow of the wellbore fluid and enable the flow of the wellbore fluid to transition to a single-phase fluid flow within the passage;

a phase composition sensor coupled to the conduit and configured to identify formation of the single-phase fluid flow within the conduit, wherein the phase composition sensor is configured to provide feedback indicative of the formation of the single-phase fluid flow to a controller; and one or more auxiliary sensors coupled to the housing and configured to provide additional feedback indicative of characteristics of the wellbore fluid to the controller, wherein the characteristics comprise pressure of the wellbore fluid, a temperature of the wellbore fluid, a flow rate of the flow of the wellbore fluid, or a combination thereof, and wherein the controller is configured to monitor a power consumption of the heating element and to determine an enthalpy of the wellbore fluid or an enthalpy flow rate of the flow of the wellbore fluid based on the power consumption, the feedback, and the additional feedback.

12. The downhole tool of claim 11, wherein the passage includes an inlet section, a converging section, and an outlet section, wherein the inlet section is configured to receive the flow of the wellbore fluid as a two-phase fluid flow, the heating element is configured to heat the wellbore fluid to transition the flow of the wellbore fluid from the two-phase fluid flow to the single-phase fluid flow, and the outlet section is configured to condense the single-phase fluid flow back to the two-phase fluid flow.

13. The downhole tool of claim 12, wherein the phase composition sensor is configured to identify the formation of the single-phase fluid flow based on identification of an interface within the inlet section that corresponds to a boundary between the two-phase fluid flow and the single-phase fluid flow.

14. The downhole tool of claim 13, wherein the phase composition sensor is a light sensor configured to measure scattering of a light beam as the light beam travels through the flow of the wellbore fluid within the conduit.

15. The downhole tool of claim 14, wherein the light sensor comprises an emitter configured to generate and project the light beam and a receiver configured to detect the light beam, and wherein identifying the formation of the single-phase fluid flow within the conduit is based on determining a reduction in light intensity between the emitter and the receiver is less than a threshold amount.

16. A method, comprising:
conveying a downhole tool into a wellbore;
directing a flow of a wellbore fluid from the wellbore through a passage of the downhole tool, wherein the wellbore fluid is a two-phase fluid when entering the passage;
heating the flow of the wellbore fluid via a heating element to transition the wellbore fluid from the two-phase fluid to a single-phase fluid;
detecting formation of the single-phase fluid within the passage via a phase composition sensor positioned near the passage;
monitoring, via a controller, a power consumption used by the heating element to transition the wellbore fluid to the single-phase fluid; and
determining, via the controller, an enthalpy of the wellbore fluid within the wellbore based in part on the power consumption and detection of the formation of the single-phase fluid.

17. The method of claim 16, comprising receiving, via one or more sensors, feedback indicative of characteristics of the wellbore fluid within the wellbore, wherein the characteristics include a temperature of the wellbore fluid, a pressure of the wellbore fluid, or both.

18. The method of claim 17, comprising determining, via the controller, the enthalpy of the wellbore fluid based on the power consumption, the detection of the formation of the single-phase fluid, and the feedback.

19. The method of claim 17, further comprising:
receiving, via one or more sensors, additional feedback indicative of a flow rate of the wellbore fluid through the wellbore or a flowrate of the wellbore fluid through the passage; and
determining, via the controller, an enthalpy flow of the wellbore fluid based on the power consumption, the detection of the formation of the single-phase fluid, the feedback, and the additional feedback.

20. The method of claim 16, comprising increasing a heat output of the heating element after lapse of a predetermined time interval until the formation of the single-phase fluid within the passage is detected.

* * * * *